(12) United States Patent
Galante

(10) Patent No.: US 9,216,121 B2
(45) Date of Patent: Dec. 22, 2015

(54) SUPPORT AND CONTAINMENT STRUCTURE FOR PERSONS

(76) Inventor: Marco Galante, Cividale Del Friuli (IT)

( * ) Notice: Subject to any disclaimer, the term of this patent is extended or adjusted under 35 U.S.C. 154(b) by 42 days.

(21) Appl. No.: 13/393,128

(22) PCT Filed: Aug. 27, 2010

(86) PCT No.: PCT/IB2010/002099
§ 371 (c)(1),
(2), (4) Date: Feb. 28, 2012

(87) PCT Pub. No.: WO2011/024061
PCT Pub. Date: Mar. 3, 2011

(65) Prior Publication Data
US 2012/0157901 A1    Jun. 21, 2012

(30) Foreign Application Priority Data
Aug. 31, 2009   (IT) ............................... UD2009A0145

(51) Int. Cl.
*A61F 5/02* (2006.01)
*A61G 5/12* (2006.01)

(52) U.S. Cl.
CPC ... *A61G 5/12* (2013.01); *A61F 5/02* (2013.01); *A61F 5/022* (2013.01); *A61G 2005/122* (2013.01); *A61G 2210/10* (2013.01)

(58) Field of Classification Search
CPC .................. A61F 5/0193; A61F 5/02–5/028; A61F 2005/01; A61F 2005/0102; A61F 2005/0132–2005/0172; A61F 5/12
USPC ................. 602/19, 5, 6, 12, 16; 128/870–871
See application file for complete search history.

(56) References Cited

U.S. PATENT DOCUMENTS

| 5,840,051 A * | 11/1998 | Towsley ........................... 602/19 |
| 6,257,664 B1 | 7/2001 | Chew |
| 2008/0021357 A1 * | 1/2008 | Firsov ............................... 602/19 |

FOREIGN PATENT DOCUMENTS

| EP | 2 070 501 A2 | 9/2010 |
| WO | WO 02/22067 A1 | 3/2002 |
| WO | WO 03/051264 A1 | 6/2003 |

OTHER PUBLICATIONS

International Search Report & Written Opinion for PCT/IB2010/002099.
Chinese Office Action from Counterpart Chinese Application No. 20108042574.5 dated Mar. 4, 2014 (7 pages).

* cited by examiner

*Primary Examiner* — Victoria J Hicks
*Assistant Examiner* — Kari Petrik
(74) *Attorney, Agent, or Firm* — Flaster/Greenberg, P.C.

(57) ABSTRACT

A support and containment structure for persons comprises at least one support member which extends mainly along a longitudinal axis, and at least one containment element. The at least one containment element is assembled transversely on the at least one support member and is able to contain the trunk of the person. The at least one support member consists of a plurality of modular elements adjacent to each other, selectively adjustable in height and able to be clamped in a stable position by means of relative clamping means. The modular elements assume, in their entirety during use, a position substantially adapted to the trunk of the person in correspondence with his spine.

11 Claims, 4 Drawing Sheets

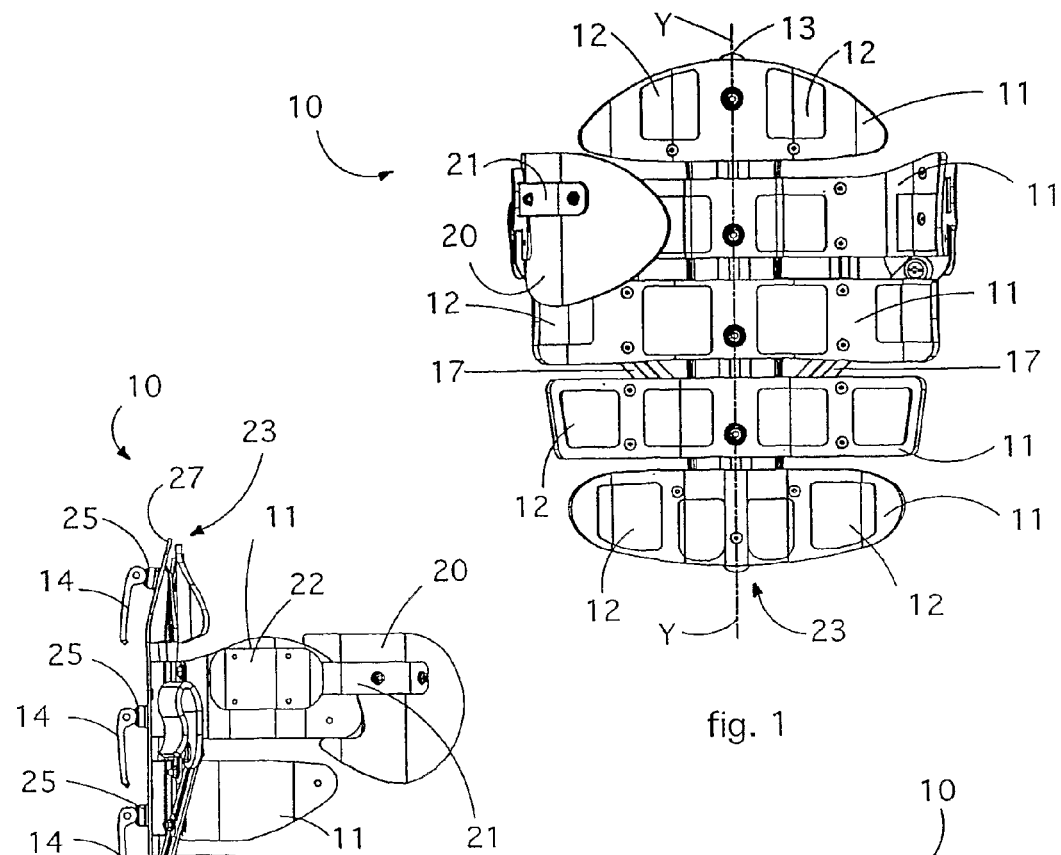
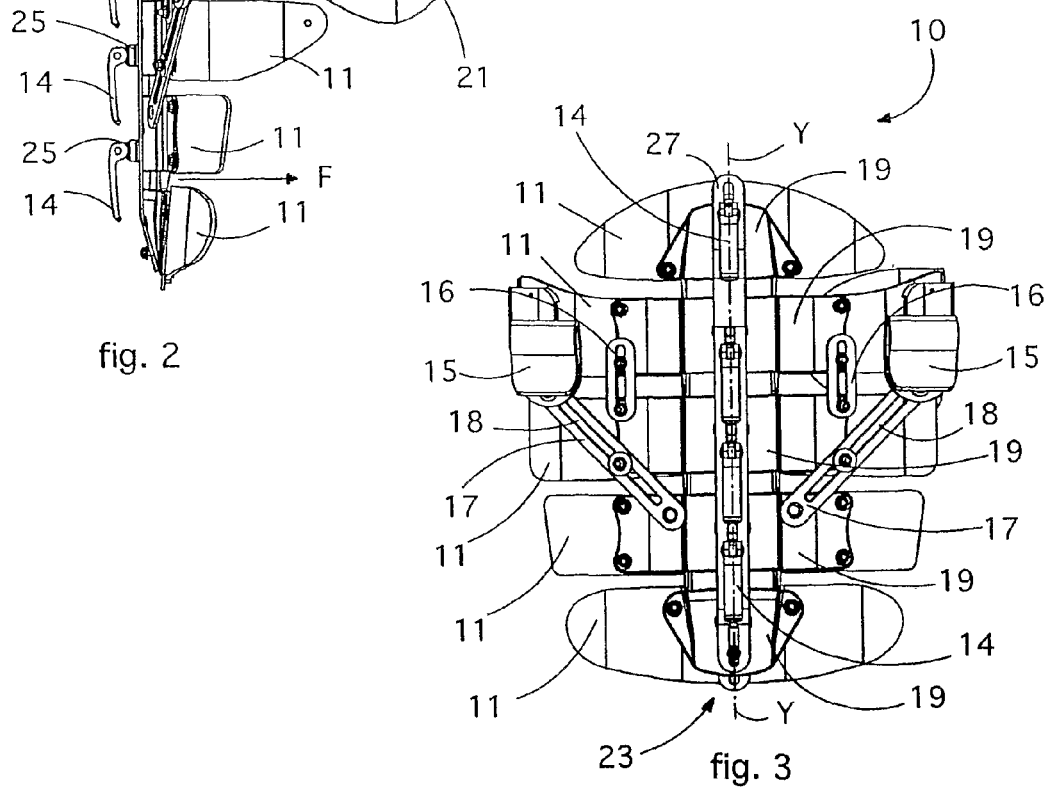
fig. 1
fig. 2
fig. 3

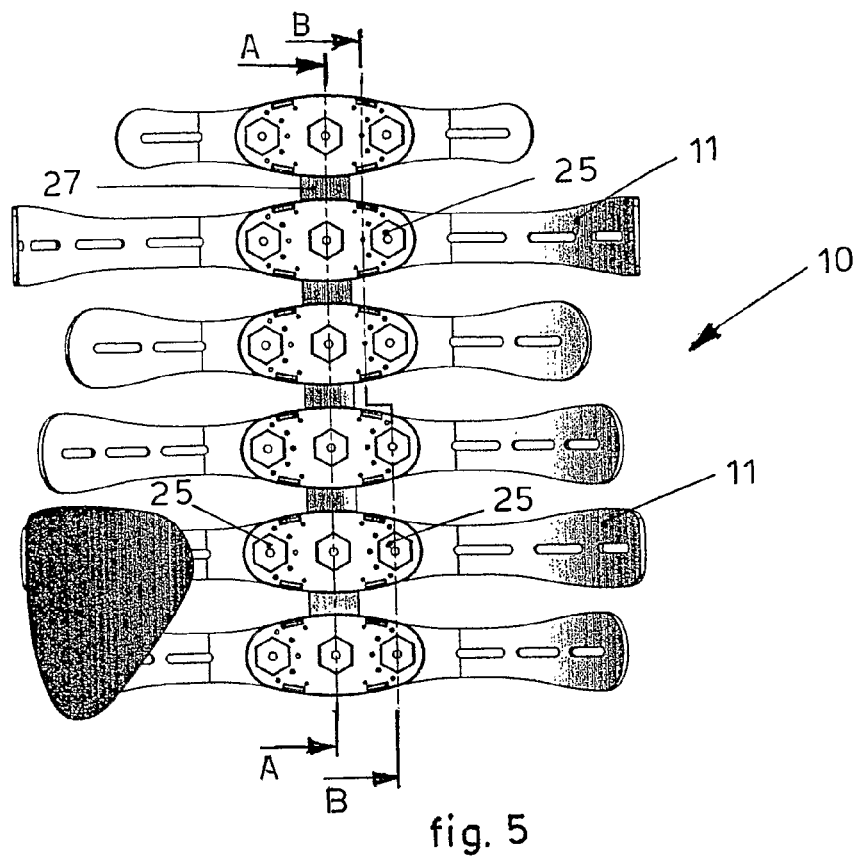
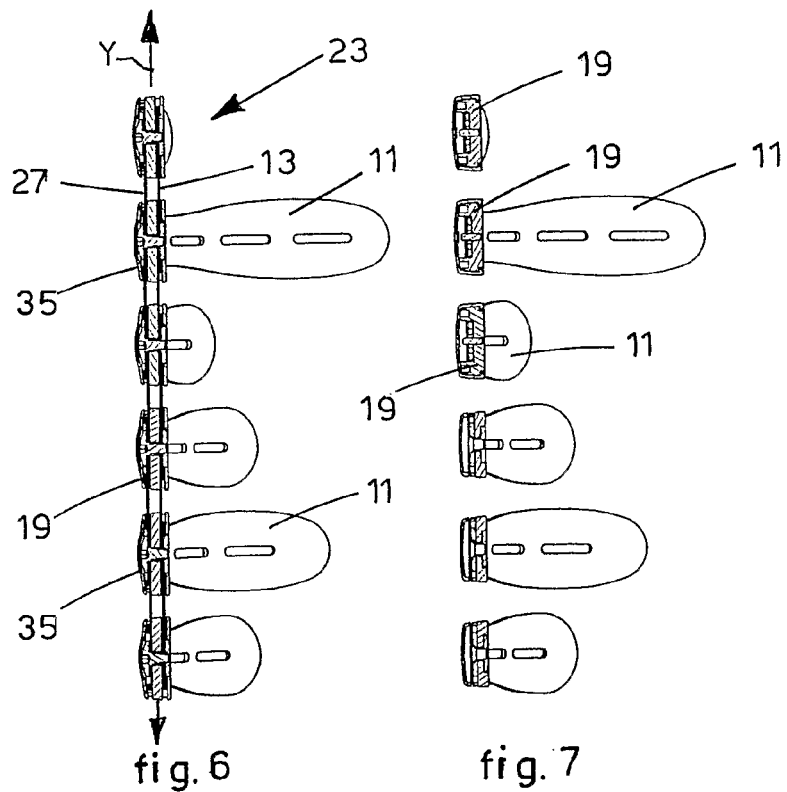

SUPPORT AND CONTAINMENT STRUCTURE FOR PERSONS

BACKGROUND OF THE INVENTION

1. Field of the Invention

The present invention concerns a support and containment structure for persons who cannot maintain an adequate and functional position of the body, such as for example the disabled.

In particular the present invention is preferably applied where a person with motor difficulties needs support, such as for example a backrest, a corset or other for his/her trunk, which is able to accompany him/her in carrying out his/her daily activities with an adequate level of flexibility

2. Description of Related Art

For people who are unable to maintain an adequate and functional position of the body, such as for example the disabled, it is known that they must be supported by an adequate support, able to guarantee a certain stability, comfort and freedom of movement so they can participate in everyday activities. Indeed, a correct posture promotes the vital functions and increases people's personal abilities.

Disabled people have different support requirements according to the type of pathology by which they are affected, and to the defects in posture that need to be compensated.

Moreover, often the disabled constantly need support structures which accompany them in their everyday activities and, according to the activity which they carry out during the day, for example eating, reading, moving, they need structures that are more or less flexible, able to adapt to individual physiological needs.

Traditional support and containment structures are known, applied for example to carriages, chairs or other, to contain the trunk or pelvis of the disabled. These structures are made with a single frame, generally of rigid plastic material, and with a standard and ergonomic shape.

Such structures are generally padded and lined with spongy material or other, so as to make them more comfortable; additional accessories can be applied so as to improve the postural functionality, depending on the requirements and type of user.

One disadvantage of this traditional solution is that it addresses only the most "standardized" pathological situations: the structure in fact has a fixed level of rigidity and poor adjustability, whether the user has a good control of his/her movements or suffers uncontrolled spasms of the body.

In the first case the disabled person would need a structure able to guarantee great flexibility, in the second case he/she would need a more rigid structure.

A support and containment structure is also known comprising a support member with a mainly longitudinal development in a single piece, able to support the spine of the disabled person during his/her movements.

This solution has the disadvantage that it cannot easily be personalized and adapted to the individual characteristics and needs of the person for whom it is intended.

This because if the central element is made of flexible material, a subsequent stiffening is not possible, and vice versa, which makes the structure unsuitable to adapt to the continuous physiological adjustments to which the trunk of a disabled person may be subjected over time.

Another disadvantage of this solution is that the central element, being fixed and non-adjustable, is not suitable for all disabled persons but only for those with more standard pathologies and with a more regular bodily structure.

Another disadvantage of this solution is the presence of a lot of warehouse pieces, which renders the management of the warehouse costly and complex.

Other known solutions, on which the improvements made by the present invention are based, are described in the documents WO-A1-02/22067 and EP-A2-2.070.501.

Purpose of the present invention is to achieve a support and containment structure for disabled persons which can be personalized and is able to adapt to every type of requirement of the users and their movements, by means of a flexible structure which allows a precise but not fixed adjustment, able to follow the little movements of the persons, assisting them and providing, where necessary, a moderate control. It is therefore the disabled person who determines the position of the various modules of the support and containment structure and the level of rigidity of the structure.

The Applicant has devised, tested and embodied the present invention to overcome the shortcomings of the state of the art and to obtain these and other purposes and advantages.

BRIEF SUMMARY OF THE INVENTION

The present invention is set forth and characterized in the independent claim, while the dependent claims describe other characteristics of the invention or variants to the main inventive idea.

In accordance with the above purpose, a support and containment structure for persons comprises at least a support member, which extends mainly along a longitudinal axis, and at least a containment element, advantageously a plurality of containment elements.

The at least one containment element is mounted transverse on the at least one support member in order to contain the trunk of the person in a personalized manner.

According to a characteristic feature of the present invention, the at least one support member consists of a plurality of modular elements selectively adjustable in height and clampable in a stable position by means of relative clamping means. The modular elements assume, all together and in use, a position substantially adapted to the trunk of the disabled person in correspondence with the user's spine.

At the moment of assembly therefore, the support member, together with the modular elements attached thereto, constitute the bearing column of the support and containment structure, whereas the transverse containment elements constitute the personalized rib structure according to the applications required on each occasion for the patient and/or the specific user.

According to a variant of the present invention, each modular element is provided with a female part and/or a male part. The female part of each modular element cooperates, at least partly, with the male part of the adjacent modular element and vice versa, so as to constitute the support member.

According to another variant, each modular element has at least laterally shaped positioning seatings for the positioning and relative anchoring of at least part of the relative transverse containment elements.

According to another variant, the transverse containment elements have a plurality of holes and/or eyelets to allow the positioning thereof, and then attachment, in a variable position with respect to the longitudinal support member.

According to another variant, the clamping means comprise at least a clamping lever or plate and at least a stopping nut to selectively clamp the modular elements in the adjusted position and at least an attachment element to prevent the at least one stopping nut from accidentally coming loose due to vibrations or other.

According to another variant of the present invention, there are two attachment elements which are disposed respectively between the containment elements and the support member to which the containment elements are attached, and between the support member and the clamping levers or plates, so as to allow a stable attachment of the modular elements to each other.

According to another variant, the two attachment elements, which can each be made in a single piece or may in turn consist of a plurality of fixed elements to constitute a single piece, have a plurality of shaped holes and/or eyelets, one for each modular element.

Each modular element of the support member is able to be disposed in a clamping position that can vary along the hole or eyelet associated therewith. A close-up position of the modular elements causes a stiffening of the support member, whereas a distanced position makes the support member more flexible.

According to another variant of the present invention, each containment element is mounted laterally on the support member by jointing.

According to another variant, each containment element is mounted on the support member by means of a hinging element.

According to another variant of the present invention, the support and containment structure comprises stiffening rings, attached transverse to at least two adjacent modular elements, able to confer greater rigidity to the structure.

According to another variant, the support and containment structure comprises hooks to assemble the structure on seating or movement means for the disabled.

According to another variant, the support and containment structure comprises at least an additional lateral support, applicable to one end of the at least one containment element in order to extend it and allow it to surround the disabled person's body more

BRIEF DESCRIPTION OF THE SEVERAL VIEWS OF THE DRAWINGS

These and other characteristics of the present invention will become apparent from the following description of a preferential form of embodiment, given as a non-restrictive example with reference to the attached drawings wherein:

FIG. 1 is a front view of a support and containment structure, showing the surface that houses the trunk of the disabled person;

FIG. 2 is a lateral view of the support and containment structure for disabled persons in FIG. 1;

FIG. 3 is a rear view of the support and containment structure for disabled persons in FIG. 1, showing the surface of the structure that rests on carriages, wheelchairs or other;

FIG. 5 is a front view of another form of embodiment of the present invention;

FIGS. 6 and 7 show respectively sections A-A and B-B of FIG. 5; and

DETAILED DESCRIPTION OF THE INVENTION

Figure 4:
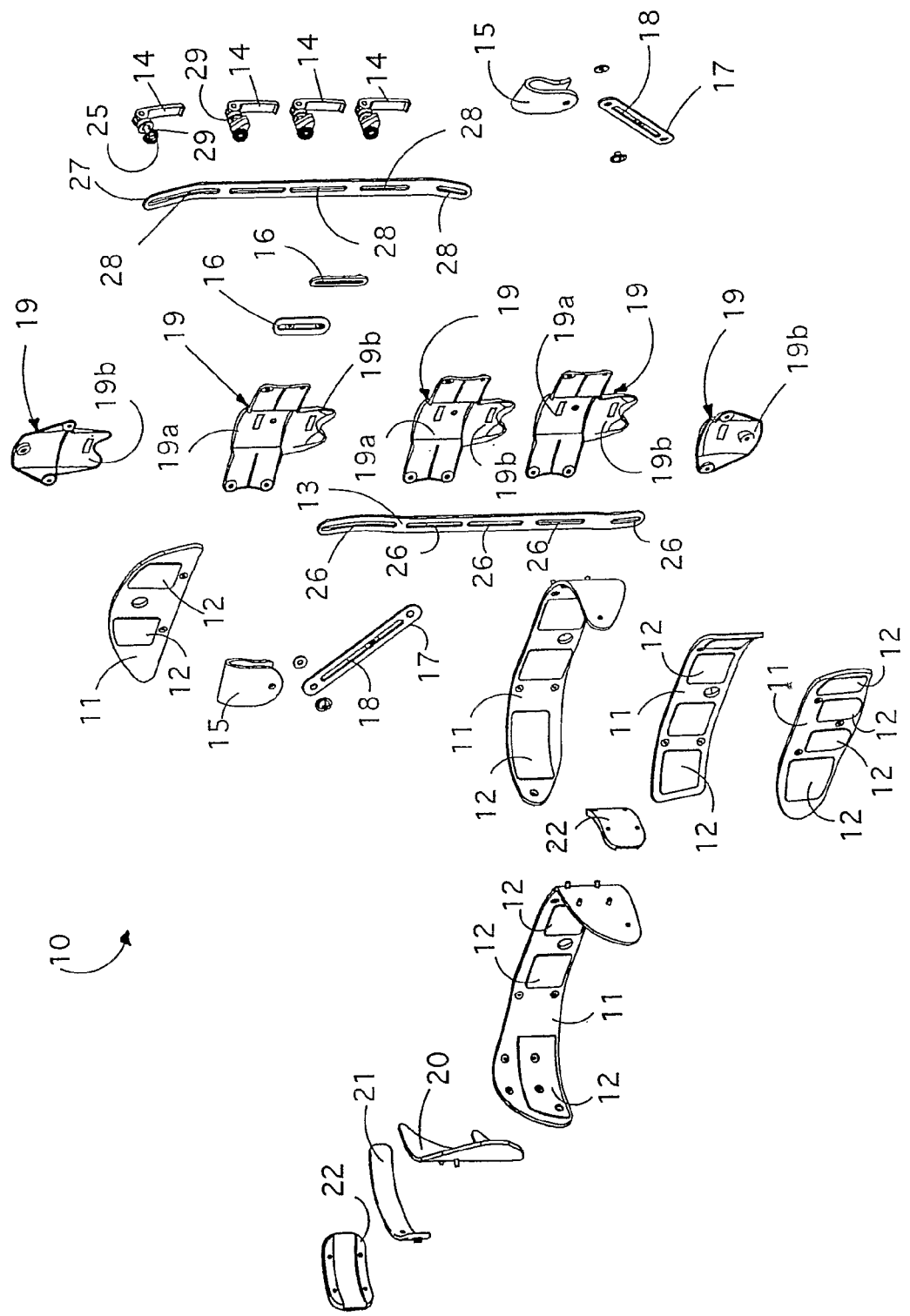
FIG. 4 is an exploded view of the support and containment structure for disabled persons in FIG. 1.

With reference to FIG. 1, a support and containment structure 10 for disabled persons comprises a support member 23, which extends mainly along a longitudinal axis Y, and a plurality of containment elements 11, disposed transverse to the support member 23 and mounted upon it, each able to contain, at least partly, specific parts of the trunk of the disabled person.

The support and containment structure 10 has a front surface, in use, shown in FIG. 1, to house the trunk of the disabled person and a rear surface, in use, shown in FIG. 3, to rest or attach the structure to walking means, transport means or other, such as for example carriages, wheelchairs, Zimmer frames etc.

In this case, the containment elements 11 have different shapes and sizes, according to the position occupied along the support member 23 and according to the part of the disabled person's trunk to be supported or contained.

Obviously they may also vary in number according to their shape and size and according to the section of trunk they have to support, according to the patient or specific user.

The containment elements 11 are also at least partly bent forward (in the direction indication by the arrow F in FIG. 2) with respect to the support member 23 so as to accommodate ergonomically a corresponding portion of the disabled person's trunk.

In this case, at one bent end of a containment element 11 an additional lateral support 20 is mounted, as shown in FIGS. 1 and 2, to provide a greater support to the disabled person's trunk.

To achieve this, an attachment element 21 is attached to the additional lateral support 20 and cooperates with an attachment element 22, located on the bent end of the element 11 to which the support 20 is applied.

Figure 8:
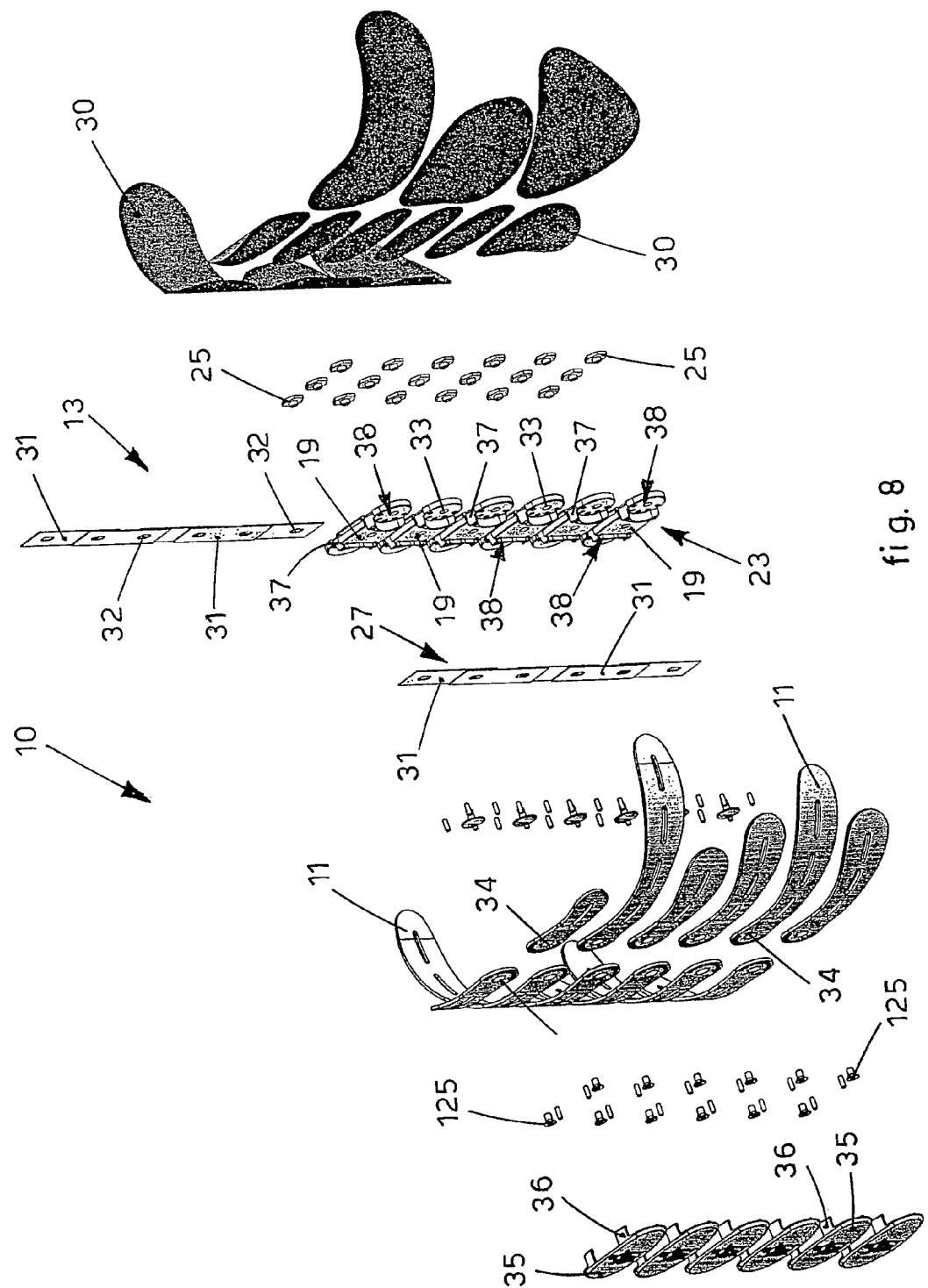
FIG. 8 is an exploded view of the embodiment in FIG. 5.

With reference to FIG. 1, each containment element 11, at the front part of the support and containment structure 10, has a plurality of Velcro surfaces 12 to allow to cover the structure 10 with padding (indicated by the reference number 30 only in the form of embodiment shown in FIG. 8) able to make it comfortable.

The support member 23, on which the containment elements 11 are mounted, is able to support the disabled person's spine, adapting to its curves.

The support member 23 consists of a plurality of modular elements 19, disposed adjacent to each other and substantially aligned in the direction of the axis Y, and assumes, in use, an overall position adapted to the person's trunk in correspondence with his/her spine.

In the embodiment shown in FIGS. 1-4, each modular element 19 is equipped with a female part and/or a male part.

The female part of each modular element 19 cooperates, at least partly, with the male part of the adjacent modular element 19 and vice versa, to form the support member 23.

The reciprocal positioning of the modular elements 19 is adjustable according to the desired level of rigidity/flexibility of the support member 23, inasmuch as the closer the modular elements 19 are disposed to each other and overlapping, the more the rigidity of the support member 23 increases.

In this case, the support and containment structure 10 for the disabled also comprises two attachment elements, respectively front 13 and rear 27, with a mainly longitudinal development, and a plurality of stopping nuts 25 and clamping levers 14, as shown in FIGS. 2 and 4.

The attachment elements 13 and 27 are provided with eyelets, respectively 26 and 28, disposed one after the other along the longitudinal direction.

The attachment element 13 is positioned between the support member 23 and the containment elements 11, whereas the attachment element 27 is disposed to the rear of the attachment element 13, between the support member 23 and the clamping levers 14.

To be more exact, on each modular element 19 of the support member 23 a containment element 11 is mounted and the attachment element 13 is interposed between them, in correspondence with an eyelet 26.

The attachment element 27 is positioned to the rear of the support member 23 and each eyelet 28 is located in correspondence with one of the modular elements 19.

The stability of the relative position of the modular elements 19 along the direction of the axis Y is guaranteed by the clamping levers 14 and the stopping nuts 25.

Each clamping lever 14 has a threaded element 29 which passes through the eyelets 28 and 26 and through suitable holes made iii the modular elements 19 and the containment elements 11 associated therewith.

The threaded element 29 cooperates with the stopping nut 25 associated with it, so as to clamp the corresponding modular element 19 in the desired position.

The attachment elements 13 and 27, clamped between the stopping nuts 25 and the clamping levers 14, prevent the nuts 25 from accidentally coming loose due to the action of vibrations.

The deliberate loosening of the nuts 25 allows to make the modular elements 19 slide inside the eyelets 26 and 28 of the corresponding attachment elements 13 and 27, to allow to vary the position of the modular elements 19 with respect to each other according to the specific requirements of the disabled person.

Moreover, each stopping nut 25 can be temporarily clamped with respect to the eyelets 26 and 28, so as to temporarily determine a reciprocal stable position of the modular elements 19 with respect to each other.

In this way it is possible to vary the level of rigidity of the structure, inasmuch as with the modular elements 19 close together there is a greater rigidity of the structure, and with the modular elements 19 distanced from each other there is a greater flexibility.

By applying to at least one pair of modular elements 19 a pair of stiffening rings 16, as shown in FIG. 3, it is possible to confer even greater rigidity on the structure 10.

Moreover, in this case, two hooks 15 are attached transverse to a pair of modular elements 19 so as to allow to assemble the structure 10 on seating and movement means for the disabled, such as for example carriages, wheelchairs, Zimmer frames or other.

The hooks 15 are attached to the pair of modular elements 19 by means of two arms 17, each longitudinally passed through by at least an eyelet 18, which also perform the function of stiffening the structure 10.

With reference now to FIGS. 5-8, another form of embodiment of the structure according to the present invention is shown. The same numbers are used to refer to identical or equivalent parts as those already described with reference to FIGS. 1-4 and will not be described further.

In the embodiment shown in FIGS. 5-8, the front 13 and rear 27 attachment elements are not made in a single piece as in the previous embodiment, but consist of a plurality of flat elements 31, attached to each other. In this way, according to the reciprocal positioning of the flat elements 31, and the number thereof, the support member 23 can be personalized to be adapted to the specific case and patient or user.

The flat elements can therefore have holes 32 which, at the moment of assembly, are positioned overlapping each other, and aligned with corresponding holes 33 present on the modular elements 19, and aligned with corresponding holes 34 present on the transverse containment elements 11. Respective front nuts 25 and rear bolts 125 are inserted through the holes 32, 33 and 34, to allow the reciprocal attachment of all the elements, to constitute the structure 10.

Each modular element 19, at its lateral ends, has shaped positioning seatings 38 for the positioning and relative anchoring of at least part of the corresponding lateral end of the relative transverse containment elements 11.

As can be seen in FIG. 8, a plate 35, equipped with attachment teeth 36, is coupled with each modular element 19, cooperating with respective grooves 37, to hide from view the attachment elements of the structure 10.

It is clear that modifications and/or additions of parts may be made to the support and containment structure 10 for persons as described heretofore, without departing from the field and scope of the present invention.

I claim:

1. A support and containment structure for persons comprising at least one support member which extends mainly along a longitudinal axis, and at least one containment element, said at least one containment element being assembled transversely on said at least one support member and able to contain a trunk of a person, said at least one support member consisting of a plurality of modular elements adjacent to each other and able to be clamped in a stable position by means of relative clamps, said modular elements assuming, in their entirety during use, a position adapted to the trunk of the person in correspondence with the person's spine, wherein said clamps comprise at least one stopping nut or bolt in order to selectively clamp the modular elements in the position adapted to the trunk of the person, and two attachment elements with a longitudinal development mating with a development of said support member and disposed, respectively, between the at least one containment element and the support member and between the support member and the at least one stopping nut or bolt, wherein the position of each modular element is adjustable such that when the modular elements are close together the support member has greater rigidity and when the modular elements are distanced from each other the support member has greater flexibility that allows for the modular elements to adapt to curves of each person's spine.

2. The support and containment structure for persons as in claim 1, wherein each modular element is provided with a female part and/or a male part, and each said female part on one modular element cooperates, at least partially, with the male part of an adjacent modular element and vice versa, so as to constitute the support member.

3. The support and containment structure for persons as in claim 1, wherein each attachment element is made as a plurality of flat elements reciprocally attachable at a moment of assembly of the support and containment structure.

4. The support and containment structure for persons as in claim 1, wherein each attachment element is made as a single piece.

5. The support and containment structure for persons as in claim 1, wherein the attachment elements have a plurality of eyelets or holes, wherein each modular element has at least one eyelet or hole, and each modular element is able to be disposed in a clamping position variable along the at least one eyelet or hole associated therewith.

6. The support and containment structure for persons as in claim 1, wherein each containment element is assembled laterally on the support member by jointing.

7. The support and containment structure for persons as in claim 1, wherein each containment element is assembled on the support member by a hinging element.

8. The support and containment structure for persons as in claim 1, wherein the support and containment structure comprises stiffening rings, attached transversally to at least two of the modular elements, able to give greater rigidity to the structure.

9. The support and containment structure for persons as in claim 1, wherein the support and containment structure for persons comprises hooks to assemble the structure on seating or movement means for the disabled.

10. The support and containment structure for persons as in claim 1, wherein the support and containment structure comprises at least an additional lateral support, applied to one end of the at least one containment element in order to extend it.

11. The support and containment structure for persons as in claim 1, wherein each modular element, at lateral ends, has shaped positioning seatings for the positioning and relative anchoring of at least part of a corresponding lateral end of the relative transverse containment elements.

* * * * *